US00PP35920P2

(12) United States Plant Patent
Barendse

(10) Patent No.: US PP35,920 P2
(45) Date of Patent: Jul. 2, 2024

(54) ***RHODODENDRON* PLANT NAMED 'AZAARE01'**

(50) Latin Name: ***Rhododendron* hybrid**
Varietal Denomination: AZAARE01

(71) Applicants: Kwekerij Arends Paterswolde B.V., Paterswolde (NL); Loviflowers BV, Moerbeke-Waas (BE)

(72) Inventor: Matthijs C. Barendse, Paterswolde (NL)

(73) Assignees: KWEKERIJ ARENDS PATERSWOLDE B.V., Paterswolde (NL), part interest; LOVIFLOWERS BV, Moerbeke-Waas (BE), part interest ( * ) Notice: Subject to any disclaimer, the term of this patent is extended or adjusted under 35 U.S.C. 154(b) by 0 days.

(21) Appl. No.: 18/101,058

(22) Filed: Jan. 24, 2023

(51) Int. Cl.
*A01H 5/02* (2018.01)
*A01H 6/36* (2018.01)

(52) U.S. Cl.
USPC ..... Plt./239

(58) Field of Classification Search
USPC ..... Plt./239
CPC ... A01H 5/02; A01H 5/00; A01H 6/36; A01H 6/364
See application file for complete search history.

(56) References Cited

U.S. PATENT DOCUMENTS

PP21,160 P2 * 7/2010 Koning ..... A01H 6/364 Plt./240

OTHER PUBLICATIONS

Canadian Food Inspection Agency, Azalea Fuji, retrieved on May 1, 2023 at https://inspection.canada.ca/english/plaveg/pbrpov/cropreport/aza/app00008084e.shtml, 4 pp. (Year: 2023).*
Floral Daily, Chelsea flower show 2022: Plant of the Year, retrieved on May 1, 2023 at https://www.floraldaily.com/article/9429520/chelsea-flower-show-2022-plant-of-the-year/, pp. 1, 18-19. (Year: 2022).*
Green Garden Azalea Starstyle Pink 2022, retrieved on May 1, 2023 at https://zielonyogrodek.pl/katalog-roslin/krzewy/13932-azalia-starstyle-pink, 7 pp. (Year: 2022).*
Gardens Illustrated RHS Plant of the year 2022 announced retrieved on Aug. 24, 2023 at https://www.gardensillustrated.com/chelsea/rhs-plant-year-2022-announced, 8 pp. (Year: 2022).*
YouTube video Plant Profile: StarStyle Azalea 2018 retrieved on Aug. 24, 2023 at https://www.youtube.com/watch?v=y6dpceNbVBs, one page. (Year: 2018).*

* cited by examiner

*Primary Examiner* — June Hwu
(74) *Attorney, Agent, or Firm* — Penny J. Aguirre

(57) ABSTRACT

A new cultivar of hybrid *Rhododendron* plant named 'AZAARE01' that is characterized by its uniform and compact plant habit, its floriferous blooming habit, its dense branching habit, its inflorescences with petals that are non-overlapping resulting in a star-shaped appearance, its clearly visible stamens and pollen, its flowers that are bright pink in color, and its leaves that are narrow and long in size.

2 Drawing Sheets

Botanical classification: *Rhododendron* hybrid.
Cultivar designation: 'AZAARE01'.

BACKGROUND OF THE INVENTION

The present invention relates to a new and distinct cultivar of *Rhododendron* plant of hybrid origin, botanically known as *Rhododendron* 'AZAARE01' and will be referred to hereafter by its cultivar name, 'AZAARE01'. 'AZAARE01' is a new cultivar of *Rhododendron* shrub grown for use as a landscape plant.

The new invention arose from an ongoing controlled breeding program in Paterswolde, The Netherlands. A goal of the breeding program was to develop hybrid cultivars of *Rhododendron* with flowers that are unique in shape and color.

The Inventor made a controlled cross in 2010 in a test garden in Paterswolde, The Netherlands between two unnamed and unpatented plants from the Inventor's breeding program: the female parent; a proprietary seedling of *Rhododendron stenopetalum* X *Rhododendron simsii*) and the male parent designated as 1118-11; a proprietary seedling of *Rhododendron simsii*. 'AZAARE01' was selected in 2016 as a single unique plant amongst the resulting seedlings.

Asexual propagation of the new cultivar was first accomplished by stem cuttings in Paterswolde, The Netherlands in 2016 under the direction the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics 'AZAARE01'. These attributes in combination distinguish 'AZAARE01' as a new and distinct cultivar of *Rhododendron*.

1. 'AZAARE01' exhibits a uniform and compact plant habit.
2. 'AZAARE01' exhibits a floriferous blooming habit.
3. 'AZAARE01' exhibits a dense branching habit.
4. 'AZAARE01' exhibits inflorescences with petals that are non-overlapping resulting in a star-shaped appearance.

5. 'AZAARE01' exhibits clearly visible stamens and pollen.
6. 'AZAARE01' exhibits flowers that are bright pink in color.
7. 'AZAARE01' exhibits leaves that are narrow and long in size.

Both parent plants of 'AZAARE01' differ from 'AZAARE01' in having less compact and more open and less uniform plant habits and inflorescences that lack the star-shaped appearance of 'AZAARE01'. 'AZAARE01' can also be most closely compared to the *Rhododendron* cultivars 'Kinku Saku' (U.S. Plant Pat. No. 17,177), 'Fuji'(U.S. Pat. No. 21,160 P2), 'AZAARE02', and 'AZAARE03'. 'Kinku Saku' and 'Furious Fujiori' are both similar to 'AZAARE01' in having flowers that are pink in color. 'Kinku Saku' differs from 'AZAARE01' in having flowers that are lighter pink in color, flower petals that are touching, and stamens and pollen that are less visible. 'Fuji' differs from 'AZAARE01' in having flowers that are smaller in size, a less uniform growth habit, and a shorter blooming period. 'AZAARE02' and 'AZAARE03' are similar to 'AZAARE01' in plant size and in having flowers that are non-overlapping. 'AZAARE02' differs from 'AZAARE01' in having flowers that are bright lilac purple in color. 'AZAARE03' differs from 'AZAARE01' in having flowers that are white in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosures include website listings by Thompson-Morgan, Benara Nurseries, Suttons, Dobies, and Promesse de Fleurs.

BRIEF DESCRIPTION OF THE DRAWINGS

The accompanying color photographs illustrate the overall appearance and distinct characteristics of the new *Rhododendron*. The plant in the photograph is 20 months in age as grown outdoors with 3 plugs in a 19-cm container in Moerbeke, Belgium.

The photograph in FIG. 1 provides a side view of 'AZAARE01' in bloom.

Figure 1:
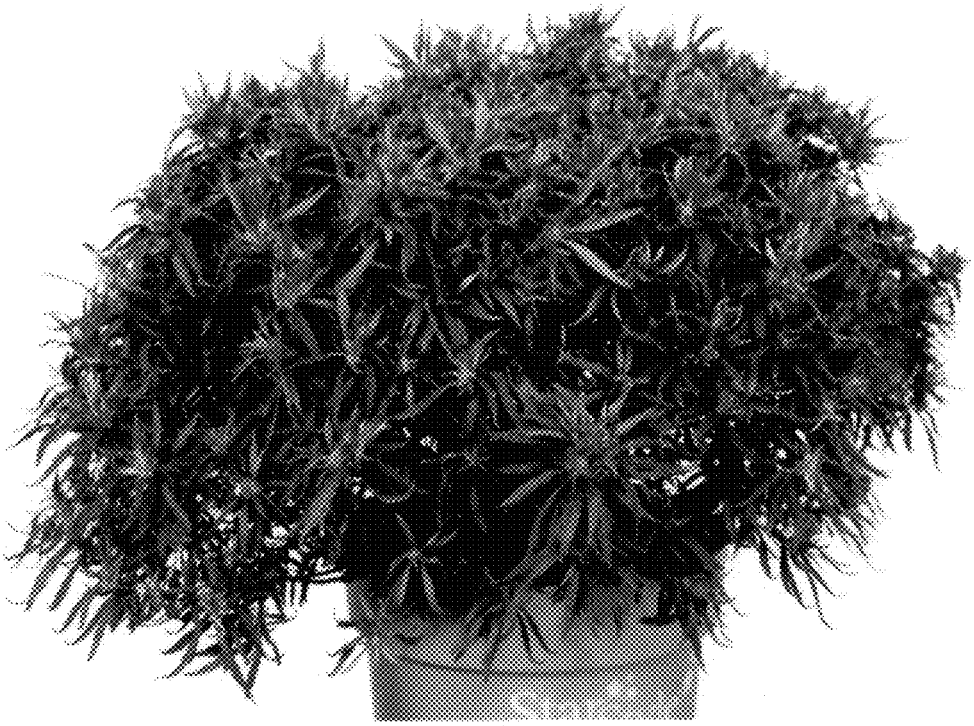
Figure 2:
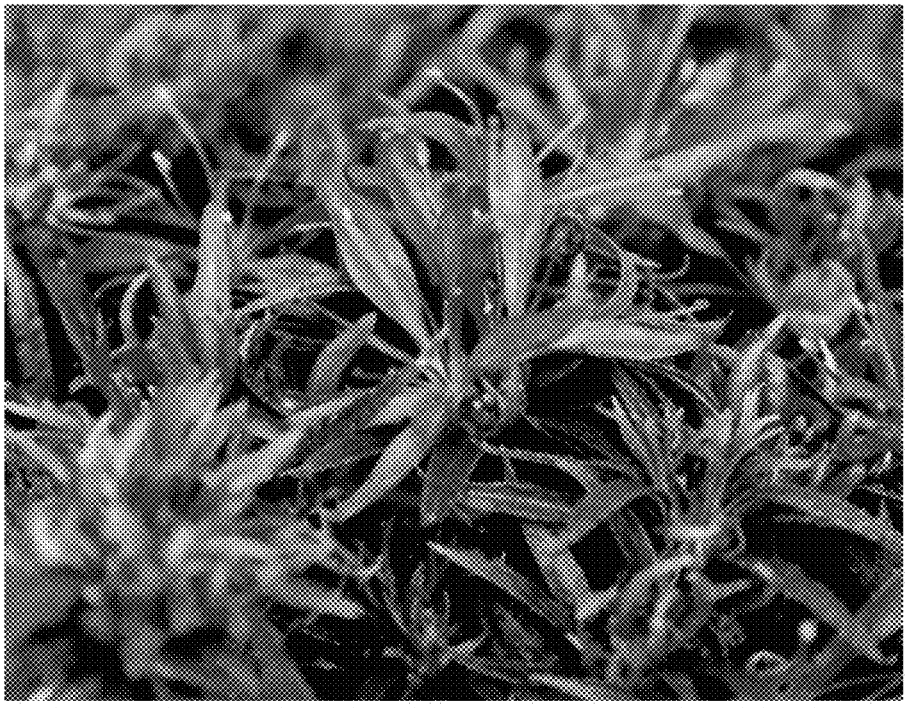

The photograph in FIG. 2 provides a close-up view of the inflorescences of 'AZAARE01'.

Figure 3:
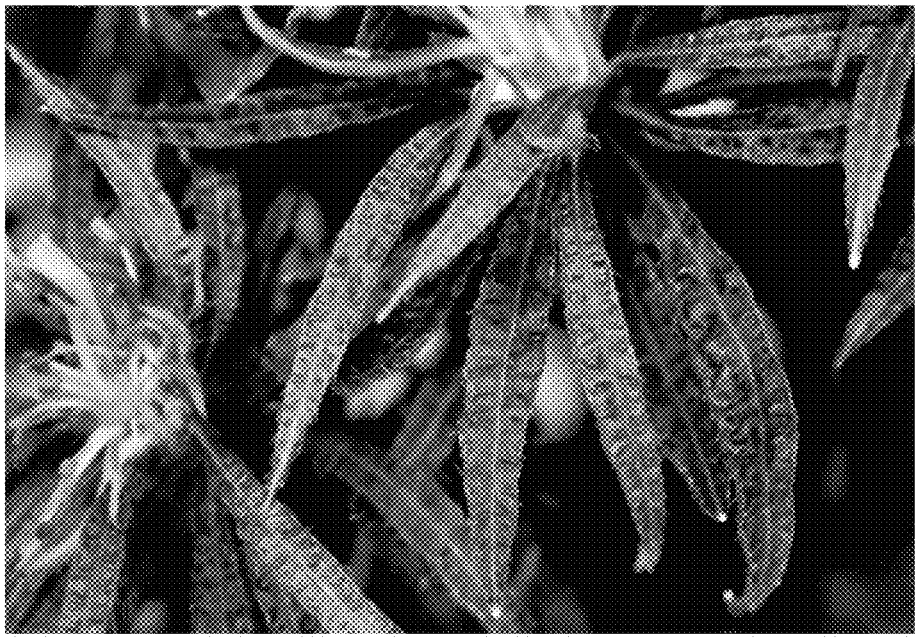

The photograph in FIG. 3 provides a close-up view of the foliage of 'AZAARE01'.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of 20-month-old plants of the new cultivar as grown outdoors with 3-plugs in a 19-cm container in in Moerbeke, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General Characteristics:

*Blooming period.*—April to May in The Netherlands.

*Plant type.*—Evergreen shrub.

*Plant habit.*—Dense, uniform growth, mounded, and compact plant habit.

*Height and spread.*—24.5 cm in height (soil level to top of foliar plane), 26.7 cm in height (soil level to top of floral plane), 39 cm in spread as grown with 3 plugs in a 19-cm container, reaches 50 cm in height and spread in the landscape.

*Hardiness.*—At least in U.S.D.A. Zones 8 to 12.

*Diseases and pests.*—No susceptibility or resistance to pests or diseases has been observed.

*Root description.*—Fibrous.

*Propagation.*—Stem cuttings.

*Growth rate.*—Moderate to high.

*Root development.*—4 weeks for root initiation and 1.5 years to produce a marketable plant from a rooted cutting.

Stem description:

*Shape.*—Round.

*Stem color.*—Young; 144A, mature; a blend of 164A and 166C, older stems and bark; 165A and 200D.

*Stem size.*—Lateral branches; an average of 5.4 cm in length, 2 mm in diameter.

*Stem surface.*—Very slightly glossy.

*Stem aspect.*—Average of 45° (varying between 40° and 50°).

*Stem strength.*—Strong.

*Branching.*—Densely branched, 10 main branches, 100 lateral branches.

*Internode length.*—5 mm.

Foliage description:

*Leaf shape.*—Narrow oblong to narrow oblanceolate.

*Leaf division.*—Simple.

*Leaf base.*—Attenuate.

*Leaf apex.*—Acute.

*Leaf venation.*—Anastomosing, upper surface; 147C in color, lower surface; N148D in color.

*Leaf margins.*—Slightly undulate.

*Leaf attachment.*—Petiolate.

*Leaf arrangement.*—Alternate, leaf clusters whorled at terminal shoot apex.

*Leaf orientation.*—Horizontal, sometimes apex curved slightly upward.

*Leaf aspect.*—Flat to very slightly wavy (lamina).

*Leaf surface.*—Both surfaces moderately rugose, lower surface matte to very slightly glossy, sparsely to moderately covered with very short hairs, 0.75 mm in length, too small to measure color, upper surface moderately glossy, margins moderately covered with short hairs 1 mm in length, too small to measure color.

*Leaf color.*—Young leaves upper surface; a blend of 143A and 146A, no anthocyanin observed, young leaves lower surface; 143B in color, mature and fall leaves upper surface; a blend of 138A and 138B, mature and fall leaves lower surface; a blend of 138A and 138B.

*Leaf size*.—Average of 3.5 cm in length, 5 mm in width.

*Petioles*.—Average of 5 mm in length and 1 mm in diameter, strong, upper surface color 145A, lower surface color N144B, both surfaces slightly glossy and moderately covered with short hairs, 1 mm in length and N170B in color.

Flower description:

*Inflorescence type*.—Axillary and terminal clusters.

*Lastingness of flowers*.—Average of 10 days.

*Inflorescence size*.—Average of 3.7 cm in height and 5.8 cm in diameter.

*Flower quantity*.—Average of 3 per inflorescence, 240 per plant.

*Flower size*.—An average of 5.4 cm in diameter and 2.5 cm in height.

*Flower fragrance*.—None.

*Flower type*.—Rotate, single.

*Flower aspect*.—Upright to outward.

*Flower bud*.—Obovate in shape, 1.3 cm in length, 9 mm in diameter, surface is smooth slightly glossy, and glabrous, 53D in color.

*Tepals*.—5, non-overlapping, whorled in 1 row, unfused, 3.2 cm in length, 6.5 mm in width, narrow lanceolate in shape, slightly carinate, apex narrow acute, base narrow attenuate, margins entire, both surfaces smooth, glabrous, non-rugose, upper surface very slightly glossy, lower surface slightly glossy, when opening upper and lower surface; 58B, fully open upper surface; 58C, veins 60D, fully open lower surface; 58C to 58D, veins 60D.

*Calyx*.—Rotate, 4.0 mm in length, 9.0 mm in diameter.

*Pedicels*.—6 mm in length, 1.75 mm in diameter, average of 25° angle to lateral branch (varying between vertical and 50°), moderately strong, 145A in color, surface is very slightly glossy and moderately covered with soft hairs, an average of 1 mm in length, N155B in color.

Reproductive organs:

*Gynoecium*.—Pistil; 1, stigmas; flattened and club-shaped, 165A to 165B in color, 1 mm in length, 1.5 mm in diameter, style; average 1.3 cm in length, color; N170C, distal end 151C, ovary; 143A in color, densely covered with soft hairs, 1.5 mm in length, NN155D in color.

*Androecium*.—Stamens; 10, filaments; 2.5 cm in length, 67A in color, anthers; dorsifixed, obovate in shape, 2 mm in length, 1 mm in width, 179B to 179C in color; pollen; 156D in color, low in quantity.

*Fruit/seeds*.—No fruit or seed observed.

It is claimed:

1. A new and distinct cultivar of *Rhododendron* plant named 'AZAARE01' as herein illustrated and described.

* * * * *